United States Patent [19]
Colgan et al.

[11] Patent Number: 5,706,082
[45] Date of Patent: Jan. 6, 1998

[54] OPTOGALVANIC SPECTROSCOPY WITH PHASE INDEPENDENT DETECTION

[75] Inventors: Michael J. Colgan, Flanders; Hans P. Lie, Berkeley Heights, both of N.J.

[73] Assignee: Alimenterics Inc., Morris Plains, N.J.

[21] Appl. No.: 815,898

[22] Filed: Mar. 12, 1997

Related U.S. Application Data

[63] Continuation of Ser. No. 645,723, May 14, 1996, abandoned.

[51] Int. Cl.$^6$ .................................................. G01J 3/30
[52] U.S. Cl. .................................................. 356/311
[58] Field of Search ................................ 356/311, 316, 356/317, 318

[56] References Cited

U.S. PATENT DOCUMENTS

| | | |
|---|---|---|
| 5,394,236 | 2/1995 | Murnick .................... 356/311 |
| 5,448,196 | 9/1995 | Kanbara et al. ............. 356/311 |

OTHER PUBLICATIONS

Randy D. May and Paul H. May, "Solid–state radio frequency oscillator for optogalvanic spectroscopy: Detection of nitride oxide using the 2–0 overtone transition," pp. 2242–2245, Rev. Sci. Instrum. vol. 57 No. 9, Sep. 1986, ©1986 American Institute of Physics.

D.E. Murnick, M.J. Colgan and F.A. Moscatelli, "Optogalvanic signals from argon metastables in a rf glow discharge," pp. 792–794, Appl. Phys. Lett. vol. 54, No. 9, Feb. 1989, ©1989 American Institute of Physics.

Primary Examiner—F. L. Evans
Attorney, Agent, or Firm—Lerner, David, Littenberg, Krumholz & Mentlik

[57] ABSTRACT

In an optogalvanic spectroscopy system, a plasma is exposed to light at a wavelength associated with a particular species in the analyte. The light is amplitude modulated. The amplitude of a modulated component in the signal representing electrical impedance of the plasma is detected in a phase independent manner, so that the detected amplitude is substantially independent of the phase of the modulated component in the impedance signal relative to the amplitude modulation of the light. The system has reduced sensitivity to changes in the spectrum of the applied light.

17 Claims, 1 Drawing Sheet ns, one at the first modulation frequency representing the
OPTOGALVANIC SPECTROSCOPY WITH PHASE INDEPENDENT DETECTION This is a continuation of application Ser. No. 08/645,723 filed May 14, 1996, now abandoned.

BACKGROUND OF THE INVENTION

The present invention relates to the art of spectroscopic analysis, and more particularly relates to the art of optogalvanic spectroscopy.

In spectroscopic analysis, the composition of a sample is measured by measuring the response of the sample to light or other electromagnetic radiation. In optogalvanic spectroscopy, the sample is maintained in an ionized, gaseous condition or "plasma", and the response of the sample is measured by measuring the change in electrical impedance of the plasma caused by the radiation.

For example, in preferred embodiments described in U.S. Pat. No. 5,394,236 of Daniel E. Murnick, optogalvanic spectroscopy can be used to determine the amounts of particular atomic isotopes present in a sample. Isotopes are different forms of the same chemical element, having an atomic nuclei of different masses. Naturally occurring carbon consists predominantly of $^{12}C$, i.e., carbon having an atomic mass of 12 atomic mass units ("amu"). Other isotopes of carbon are $^{13}C$ and $^{14}C$ having masses of 13 or 14 a.m.u. respectively. $^{14}C$ is radioactive, whereas $^{13}C$ and $^{12}C$ are stable, nonradioactive materials.

In preferred methods taught in the '236 patent, a sample which includes carbon dioxide molecules or ions containing different isotopes is maintained in a plasma, so that the molecules or ions are present in excited states. Electrons in the excited molecules and ions constituting the plasma can occupy numerous energy levels. The amount of energy absorbed or released when an electrons moves between two energy levels is referred to as the transition energy between the two levels. The transition energies of species such as molecules and ions depend on the composition of the species. Thus, excited species which include different elements, or different isotopes of the same elements, will have different transition energies. The energy of the applied radiation is inversely related to its wavelength. The applied radiation will interact with the plasma, and will trigger a particular transition in the excited species, when the energy of the applied radiation matches the transition energy of that transition. Radiation such as light in two wavelength bands is directed through the plasma. Light in a first wavelength band matches a transition energy associated with excited species including $^{12}C$ and thus interacts with the excited species including $^{12}C$. Because this light does not match a transition energy associated with species including $^{13}C$, it does not interact substantially with the excited species including $^{13}C$. Light in the second wavelength band interacts with the excited species including $^{13}C$ and not with those including $^{12}C$. By measuring the optogalvanic response of the analyte to the applied radiation in the different wavelength bands, one can determine the amounts of the different isotopes present in the sample.

As also disclosed in the '236 patent, the light may be provided by lasers. The amplitude of the light in each wavelength band is varied at a different modulation frequency. For example, light in a wavelength band associated with $^{12}CO_2$ may be turned on and off at a first modulation frequency, whereas light in a wavelength band associated with $^{13}CO_2$ may be turned on and off at a second modulation frequency. The electrical signal representing the electrical impedance of the plasma includes two separate components, one at the first modulation frequency representing the amount of $^{12}CO_2$ and another at the second modulation frequency representing the amount of $^{13}CO_2$. These can be electronically separated from one another and measured to provide a pair of signals which represents the relative amounts of the two isotopes. For example, the two components can be captured by separate lock-in amplifiers. Each lock-in amplifier is arranged to select only a component of the electrical impedance signal varying in synchronism with the modulation of the light source at a particular modulation frequency. In effect, the lock-in amplifier multiplies the impedance signal by a gain factor, and the gain factor varies in synchronism with the modulation of the applied light at one modulation frequency. In the resulting signal, components which are synchronized with modulation of the applied light are enhanced, whereas components which are not synchronized with the modulation are suppressed. The amplitudes of the components captured by each lock-in amplifier represents the degree of interaction between light in one wavelength band and the sample. The ratio of $^{13}C$ to $^{12}C$ in the sample can be determined by comparing these amplitudes with one another.

The preferred methods according to the Murnick '236 patent provide numerous advantages over other methods used for determining the amount of different isotopes in a substance. Methods and apparatus according to the '236 patent can be reapplied to many different analytes for many different purposes. However, one especially useful application of these methods is in medical testing. Various medical and scientific procedures require determination of the relative amounts of different isotopes.

However, still further improvements would be desirable. Changes in the spectral composition of the light applied by the lasers produce changes in the measured amplitudes of the components in the impedance signal. This effect can be suppressed by controlling the lasers to assure that the light emitted by each laser has a substantially constant spectrum. However, it would be desirable to reduce the sensitivity of the system to variations in the spectra of the lasers. Such reduction in sensitivity would allow greater variation in operation of the lasers while maintaining the same degree of accuracy or, conversely, would provide even greater accuracy with the same degree of control of the spectra of the lasers.

SUMMARY OF THE INVENTION

One aspect of the present invention provides methods of determining the composition of an analyte. A method in accordance with this aspect of the invention desirably includes the steps of maintaining the analyte in gaseous form in an electrical discharge, as by maintaining the analyte in a plasma, and applying first radiation to the analyte in the discharge so that the radiation interacts with a first species in the analyte to produce an optogalvanic effect. The method also includes the step of monitoring electrical impedance of the discharge and providing an impedance signal representing the impedance. The amplitude of the first radiation is periodically varied at a first modulation frequency. The method according to this aspect of the present invention may include the step of detecting the amplitude of a first component in the impedance signal varying at a first component frequency equal to the first modulation frequency or a harmonic thereof. The detected amplitudes constitutes a first value representing the amplitude of optogalvanic effect produced by the first radiation. Thus, the first value represents the amount of the first species in the analyte.

Most preferably, in accordance with this aspect of the invention, the step of detecting the amplitude of the first component is performed so that the first value is substantially independent of the phase of the first component relative to the phase of the periodic variation in amplitude of the first radiation. In a particularly preferred arrangement, the detecting step includes the step of correlating the first component in the impedance signal with a pair of correlation signals varying at the first component frequency. The correlation signals are in quadrature with one another, i.e., delayed relative to one another by one-fourth of a complete period. Correlation of the first component with one signal provides a correlated signal, referred to as the "real" correlated signal, whereas correlation of the first component with the other correlation signal provides another correlated signal, referred to as the "imaginary" correlated signal. In this preferred arrangement, the detecting step further includes the step of determining the average amplitudes of the real and imaginary correlated signals to provide real and imaginary magnitudes and combining these magnitudes with one another to provide the first value. The step of combining the magnitudes can include the step of squaring the real magnitude, squaring the imaginary magnitude, summing the squares and taking the square root of the resulting sum as the first value. The first value calculated in this manner is substantially independent of the phase of the impedance signal.

Preferred methods according to this aspect of the invention are less sensitive to variations in the spectrum of the first radiation than comparable methods using a phase-dependent detection scheme such as a simple lock-in amplifier operating in synchronism with the modulation of the applied light. Although the present invention is not limited by any theory of operation, it is believed that some of the sensitivity observed heretofore was attributable to differences in the signs of the optogalvanic signals arising from different transitions in the analyte. A single species may have many transitions with transition energies very close to one another. For example, $^{12}CO_2$ has numerous transition energies close to one another, whereas $^{13}CO_2$ has numerous transition energies which are close to one another, although quite far from the transition energies of $^{12}CO_2$. It is believed that the impedance signal arising from transitions of a particular species having slightly different transition energies will have opposite phase relative to the phase of the modulation in the applied radiation. If the applied radiation triggers one transition, the component in the optogalvanic signal representing interaction with that species will vary in synchronism with the variation in amplitude of the applied radiation. If the applied radiation triggers another transition of the same species, the optogalvanic signal representing the interaction with the same species will be directly opposite in phase to modulation of the applied radiation. It is believed that small variations in the wavelengths of the applied radiation have caused changes in the degree to which the applied radiation interacts with the different transitions of a particular species. It is further believed that this effect causes the phase of the optogalvanic signal to vary with variations in the spectrum of the applied radiation. However, regardless of the theory of operation, detection of the amplitude of a component in the optogalvanic signal in a manner which is insensitive to the phase of that component reduces the degree to which the detected amplitude varies in response to variations in the spectrum of the first radiation.

Particularly preferred methods further include the step of applying second radiation to the analyte in the discharge so that said second radiation interacts with a second species in said analyte to produce an optogalvanic effect, and periodically varying the amplitude of said second radiation at a second frequency, whereby said impedance signal will include a second component representing the change in impedance caused by the interaction between the second said impedance and varying at said second frequency. Preferably, the second frequency is different from the first frequency, and the second radiation is applied simultaneously with the first radiation. Methods according to this aspect of the invention desirably include the step of detecting the amplitude of said second component to provide a second value representing said amplitude of said second component, whereby said second value represents the amount of said second species in said analyte. The step of detecting the second component is performed so that said second value is substantially independent of the phase of said second component relative to the phase of said periodic variation in amplitude of said second radiation.

Most preferably, the first and second species are multiatomic species. The first and second species may have the same chemical composition, but may include different isotopes of the same element. For example, the first and second species may be carbon dioxide moieties including different isotopes, such as $^{13}CO_2$ and $^{12}CO_2$ moieties.

Further aspects of the invention include apparatus suitable for performing the methods as discussed above.

DETAILED DESCRIPTION OF THE PREFERRED EMBODIMENTS

Figure 1:
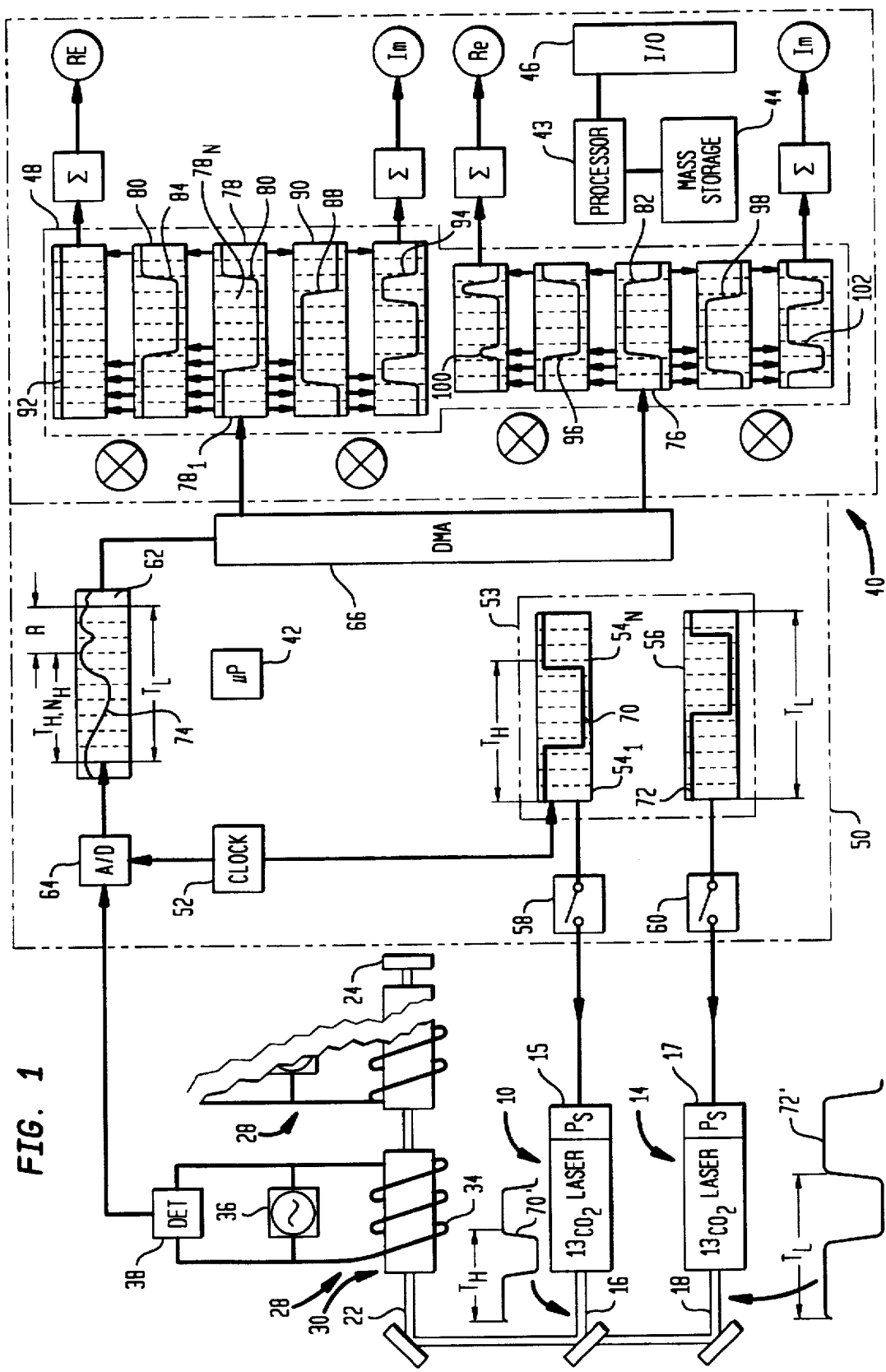
FIGURE 1 is a diagrammatic view depicting components of a system in accordance with one embodiment of the invention.

Apparatus in accordance with one embodiment of the invention includes a first laser 10. Laser 10 includes conventional components such as a tube for containing a gas mixture, electrodes arranged to create an electrical discharge within the tube and optical components such as Brewster or polarizing windows and a partially reflective output mirror together with a power source 15 for actuating the electrical discharge. The tube of laser 10 is filled with a mixture including $^{13}CO_2$ in a carrier gas such as a helium and nitrogen mixture. The optical components of laser 10 are arranged so that light in a first band of wavelengths encompassing a transition energy of excited-state $^{13}CO_2$ ions will be amplified. For example, laser 10 can be arranged to amplify light at about 11200 nm wavelength. The apparatus also includes a second laser 14, similar to laser 10. The tube of laser 14 is filled with a mixture containing $^{12}CO_2$ in the carrier gas. Its optical components are arranged to amplify light within a second band of wavelengths encompassing at least one transition energy of excited-state $^{12}CO_2$ ions. For example, the second laser 14 may be adapted to amplify light at about 10600 nm. Thus, first laser 10 is arranged to emit a beam of light 16 in the first band of wavelengths associated with $^{13}CO_2$, and is arranged to vary the amplitude of the light in such beam in accordance with a control signal supplied to an input of its power source 15. Likewise, the second laser 14 is arranged to emit a beam 18 of light in the band of wavelengths associated with $^{12}CO_2$ and to vary the amplitude of light in such beam according to a control signal applied to the input of the power source 17 included in the second laser.

An optical system 20 is arranged to combine beams 16 and 18 into a single beam 22 and to direct beam 22 along a predetermined beam path to a reflecting mirror 24. The optical components may include generally conventional mirrors together with combining optics which may incorporate a partially transmissive, partially reflective element. The optical components, including the partially transmissive element may be adapted to attenuate the light in beam 18, associated with the $^{12}CO_2$ transition energies to a greater degree than the light in beam 16, associated with $^{13}CO_2$.

The apparatus also includes several sample units 28. Each sample unit includes a chamber 30 having substantially transparent end walls arranged along the path of combined beam 22. The chambers 30 of the various sample units 28 are arranged in series, along beam path 22, so that light in the beam can pass through all of the chambers in sequence to reflecting mirror 24 and back from the reflecting mirror 24 in the reversed sequence. Ports, valves and other features (not shown) may be provided for loading analytes into chambers 30. Each sample unit 28 also includes an excitation coil 34 encircling the chamber 30 and an AC potential source 36 connected to the coil 34, together with a sensing unit 38 connected to coil 34. Excitation signal generator 36 and coil 34 are arranged to apply radio frequency ("RF") energy within chamber 30, to thereby convert any analyte in the chamber to a plasma. The sensing unit is arranged to monitor the current and voltage in coil 34, and to provide a signal representing the electrical impedance of a plasma within the chamber 30. For example, sensing unit 38 may be arranged to detect variations in impedance occurring at the amplitude modulation frequency of the RF excitation. Excitation and sensing systems of this type are well-known in the art of laser optogalvanic spectroscopy, and are described, for example, in the article Solid State Radio Frequency Oscillator for Optogalvanic Spectroscopy:Detection of Nitric Oxide Using the 2-0 Overtone Transition, by R. D. May and P. H. May, Reviews of Scientific Instrumentation, Vol. 57, No. 9, pp. 2242–2245 (1986) the disclosure of which is hereby incorporated by reference herein.

The apparatus further includes a digital computer 40 of a conventional type such as a conventional personal computer incorporating conventional elements such as a microprocessor 43, mass storage elements 44 such as tapes or disks and standard input/output devices 46 such as a keyboard screen and printer, as well as other conventional components The computer typically is equipped with a standard data bus, such as an EISA (Expanded Industry Standard Architecture) bus for transfer of signals between the elements of the computer.

The computer is equipped with a digital signal processor ("DSP") unit 50. DSP unit 50 includes a clock 52 together with a multi-bit output buffer 53 linked to switches 58 and 60. The DSP unit further includes several serial input registers 62, of which only one is depicted. Input register 62 is linked to an analog-to-digital ("A/D") converter 64. Each other input register is equipped, with a similar A/D converter. Buffer 53 is a multi-bit unit, arranged to hold digital words of 16 bits each, and to "clock out" these words in sequence responsive to signals from clock 52. Buffer 53 is connected so that a preselected bit of each word is directed to switch 58, whereas another preselected bit of each word is directed to switch 60. Thus, buffer 52 acts as two single-bit output buffers 54 and 56 operating in synchronism. Output buffer 54 and the associated switch 58 are arranged so that a series of binary 1 and 0 values representing an on/off signal stored in successive locations within output buffer 54 can be read out from the buffer in sequence, at a rate set by clock 52 and converted into an on/off signal. Switch 58 is connected to the signal input of the power source 15 of first laser 10. Similarly, buffer 56 and switch 60 are arranged so that a series of binary values representing another signal can be read out from buffer 56 and converted to an on/off signal, which in turn is supplied to the power supply 17 of laser 14.

A/D converter 64 is arranged to capture samples of the analog impedance signal 38 from sensing unit 38a in sample unit 28a at intervals set by clock 52 and to write a digital value representing each such sample into a location in buffer 62 so that the buffer is filled with a series of digital values representing successive samples of the analog signals. DSP unit 50 further includes random access memory (RAM) 48, a microprocessor 42 and a conventional direct memory access (DMA) device 66 arranged to copy the contents of serial input buffer 62 into designated locations of RAM 48 as commanded by processor 42 and to copy data from RAM 48 to output buffers 54 and 56, also as commanded by processor 42. DSP unit 50 may be a conventional unit of the type sold under the designation CAC-32a V2 by the Communication, Automation and Control company of Allentown, Pa., together with a conventional external I/O card incorporating the A/D converters and switches. Other conventional, commercially available DSP units incorporate these elements on a single card.

In a method according to one embodiment of the invention, a series of binary values representing a first modulation signal 70 are stored in first output buffer 54. First modulation signal 70 is a square wave or on/off sequence having a first frequency $f_h$ and a period $t_h$. The first frequency desirably is between about 60 and about 1000 Hz and most preferably about 100 Hz. Although the first modulation signal is represented as a line superposed on buffer 54, it should be appreciated that the signal at this stage is stored as a series of binary numbers, each in one storage position of buffer 54. Each binary number represents the value of signal 70 at a discrete time. The value in the first storage position 544 of buffer 54 represents the value at the beginning of a cycle, whereas the value in the $n^{th}$ position $54_n$ represents the value at a time corresponding to $nt_s$ where $t_s$ is the sampling interval used in the system. Similarly, a second modulation signal 72 having a somewhat lower frequency $f_l$ and a period $t_l$ is stored as a series of binary values in buffer 56. Preferably, $f_l$ is not an integral multiple of $f_h$. SFor example, $f_h$ may be 97 Hz whereas $f_l$ may be 79 Hz. Samples of a gas to be analyzed for content of $^{13}CO_2$ and $^{12}CO_2$ are provided in the sample chambers 30 of sample units 28.

Under the control of processor 42, clock 52 actuates buffer 53 (single bit buffers 54 and 56) to read out the values representing modulation signals 70 and 72, and to supply signal 70 to the power supply of laser 10, while simultaneously supplying signal 72 to the power supply of laser 14. Accordingly, first laser 10 provides beam 16 incorporating light in the first wavelength band associated with $^{13}CO_2$. This light has an amplitude varying from low to high substantially in accordance with first modulation signal 70, at frequency $f_h$ and with period $t_h$. Likewise, the light in beam 18, in the second band of wavelengths associated with $^{12}CO_2$, varies substantially in accordance with modulation signal 72 and thus varies at frequency $f_l$ and with period $t_l$. The actual variation and amplitude of the laser light may vary slightly from the applied modulation signal. For example, the light amplitude of the laser typically does not vary instantaneously and hence the square waveform of the original modulation signal will be rounded somewhat in the actual amplitude variation.

The combined light beam 22 includes the light in both bands of wavelengths, varying at both frequencies. As the light passes through the sample in chamber 30 of sample unit 28a, the light in the first band of wavelengths from laser 10, varying at frequency $f_h$ interacts with excited $^{13}CO_2$ moieties in the analyte within chamber 30a, but does not substantially interact with $^{12}CO_2$ moieties. Thus, the light in the first band of wavelengths induces an optogalvanic effect in the plasma and hence causes the impedance of the plasma to vary at the higher frequency $f_h$. Similarly, the light in the second band of wavelengths from laser 14 interacts with excited $^{12}CO_2$ moieties in the analyte and induces an optogalvanic effect varying at the lower frequency $f_l$. Accordingly, the impedance of the plasma, and the impedance signal generated by sensing unit 38a varies. The variation in the impedance signal includes a component varying at the first, higher frequency $f_h$ and having first period $t_h$. The amplitude of this first component is directly related to the amount of $^{13}CO_2$ in the analyte. The impedance signal also includes a component varying at the second, lower frequency $f_l$ and having second period $t_l$. The amplitude of this second component is directly related to the amount of $^{12}CO_2$ in the analyte.

Clock 52 actuates A/D converter 64 to capture successive samples of the impedance signal from sensing unit 38a and to write these samples in digital form into successive locations in buffer 62. The impedance signal 74 is shown as a curve superposed on the various storage locations in buffer 62. Here again, however, the signal is actually stored as a series of digital values, each representing the instantaneous amplitude of the signal at a time offset from the last previous sample by the sampling interval $t_s$.

Processor 42 of the DSP unit assigns a first set of storage locations 76 in RAM 48 for storage of an average first component signal and assigns a second set of storage locations 78 for storage of an averaged second component signal. Set 76 includes a number of storage locations $N_h$ corresponding to the number of samples representing one complete period of the first modulation signal 70. $N_h$ is equal to $t_h/t_s$. Set 78 includes a larger number of storage locations $N_l$, where $N_l = t_l/t_s$. This number of storage locations represents exactly one complete period of the lower frequency modulation signal 72. Although these and other sets of storage locations are depicted in the drawings as contiguous blocks of locations for clarity of illustration, it should be appreciated that the physical locations constituting sets of storage locations are assigned by the operating system software of the computer, and may or may not be physically contiguous. At the beginning of the process, each set of memory locations is initialized by setting all of the stored values therein to zero. At intervals corresponding to the period $t_l$ of the lower frequency modulation signal, processor 42 actuates DMA interface 66 to capture a series of $N_l$ samples from buffer 62, to add each of these samples to the contents of one location in set 76 and to add each of these samples to the contents of one location in 78.

The addition to the location of sets 78 is straightforward. Thus, the first sample in each group of samples transferred is always added to the first location $78_1$ and the $n^{th}$ sample from each transferred group is always added to the value previously stored in the $n^{th}$ location $78_n$ within set 78. In this way, the sample values added to each location within set 78 will be sample values taken at times delayed from one another by an integral number of periods $t_l$ of the low frequency component. Stated another way, each location will accumulate sample values representing the same point in the waveform of the low frequency component. The accumulated sample values represent the instantaneous value of the low frequency component associated with $^{12}CO_2$, averaged over numerous cycles. These values cooperatively define a digital representation of the low frequency component 80 in the impedance signal.

Because the number of sample values $N_l$ captured in each cycle of DMA interface 66 is unequal to the number of locations $N_h$ constituting set 76, a different scheme is used in this case. Thus, the computer, maintains an index value I denoting the point in set 76 where the first value in an incoming group of values from buffer 62 should be copied. At the beginning of the process, the index value I is equal to 1 and hence the first group of sample values is added into locations within said 76 beginning from the first such location and beginning and from the first sample value. The first $N_h$ sample values in the incoming group of sample values, representing one complete period $t_h$ of the high-frequency component is copied into the $N_h$ locations constituting set 76. This leaves R sample values remaining, where $R = N_l - N_h$. These remaining sample values represent the beginning of the next period of the high frequency component. Thus, the first one of these remaining sample values (value $N_{h+1}$) is added into the first location in set 76 and succeeding values are again added into succeeding positions in set 76 until the last value in the transferred group is added into the location (R+1) in set 76. Processor 42 increments the index I by R on each cycle of DMA interface 66. Thus, on the second cycle of the DMA interface, the first value in the transferred group will be added into location (R+2) in set 76 and so on. Whenever I is greater than or equal to $N_h$, $N_h$ is subtracted from I.

Stated another way, after each cycle of data transfer, the old value of I is replaced by a new value of I calculated according to the equation:

$$I_{new} = (I_{old} + R) \, modulo(N_h) \tag{1}$$

On each cycle of data transfer, the computer adds the first value in the group transferred from buffer 62 to the $I^{th}$ location in location set 76 and adds successive values to succeeding locations in the memory set until the last ($N_h$) location is reached whereupon the computer begins with the first location $76_1$. In this way, each location within location set 76 receives sample values delayed from one another by $N_h$ sample values, i.e., delayed from one another by a full period $t_h$ of the high frequency component.

As the system adds new values to the memory locations in sets 76 and 78, it keeps track of the number of values which have been added. After the values have been added, the accumulated value in each location is divided by the number of values which have been added. The system thus accumulates a set of averaged sample values representing an average cycle of the high frequency component 82 in memory location set 76, and accumulates a set of averaged sample values representing an average cycle of the low frequency component 80 in memory location set 78. The averaging process to form the averaged sample value set representing the low frequency component 80 tends to eliminate noise and signal components at components other than the lower modulation frequency $f_l$ and harmonics thereof. In particular, the averaging process tends to eliminate the high-frequency component at frequency $f_h$. Again, $f_h$ is not an integral multiple of $f_l$. Conversely, the averaging process used to provide the high-frequency component sample value set 82 tends to eliminate the low-frequency component $f_l$ and other noise and signal components at frequencies which are not integral multiples of $f_h$.

The computer system stores a real low-frequency correlation signal 84 as another set of digital values in a set of $N_l$ memory locations 86. Real correlation signal 84 is a sine wave have frequency equal to $f_1$, the fundamental frequency of the low frequency modulation signal 72. The system also stores a further so-called "imaginary" low-frequency correlation signal 88 in a further set of $N_l$ memory location 90. Imaginary signal 88 is the same as real signal 84, but offset by one-quarter of the signal period $t_l$. That is, the same series of digital values which define real correlation signal 84 is used to define the imaginary correlation signal 88 but the values in signal 88 are recorded beginning in location ($N_l$/4) of set 90, whereas the values constituting the real correlation signal 84 are recorded beginning at the first location in location set 86. The system calculates a real correlated signal 92 as a series of digital values by multiplying each value in the low-frequency average value set 80 by the corresponding value in the real correlation signal 84. That is, the digital value stored in the $n^{th}$ location with location set 78 is multiplied by the value stored in the $n^{th}$ location in a location set 86 to provide an $n^{th}$ correlated value. In this way, the averaged sample value associated with a given time during the period of the low-frequency component is multiplied by a correlation value associated with the same time during the period of the real correlation signal. The correlated values calculated in this way constitute a real correlated signal 92. In the same way, each averaged sample value in the low-frequency average value set 80 is multiplied by the corresponding value in the imaginary correlation signal 88. That is, the value stored in the $n^{th}$ location in set 78 is multiplied by the value stored in the $n^{th}$ location of set 90. Stated another way, each average sample value, associated with a particular time in the low-frequency averaged waveform is multiplied by a value of the imaginary correlation signal 88 associated with the same time. This process yields a set of imaginary correlated values 94 constituting an imaginary correlated signal. The real correlated signal values 92 are summed by processor 42 to give a real magnitude Re, whereas the imaginary correlated signal values 94 are separately summed to give an imaginary magnitude Im. The real and imaginary magnitudes are combined with one another by calculating $$V=\sqrt{Re^2+Im^2} \quad (2)$$

The resulting value V represents the amplitude of the averaged, low-frequency component 80 hence represents the amplitude of the low-frequency component in the impedance signal from detector 38. This amplitude varies directly with the amount of $^{12}CO_2$ in the analyte within chamber. The value of V is entirely independent of the phase of signal 80 and hence independent of the phase of the low-frequency component relative to the low-frequency modulation signal 72. Thus, the dual correlation process, coupled with the combining process results in an amplitude value which is phase-independent.

In exactly the same way, the computer maintains a set of sample values constituting a real high-frequency correlation signal 96 and an imaginary high-frequency correlation signal 98 offset from signal 96 by one-fourth of the period $t_h$ of the high-frequency signal. These signals are sine waves having frequency equal to $t_h$. Likewise, the system multiplies each value in the averaged, high-frequency signal 82 by the value in the real high-frequency correlation signal 96 corresponding to the same time to yield a set of real, correlated, high-frequency values 100 constituting a high-frequency real correlated signal. The system similarly multiplies the value in the averaged high-frequency signal 82 by the imaginary high-frequency correlation signal 98 to yield a set of values constituting an imaginary high-frequency correlated signal. The system sums all of values in signal 100 to provide a real magnitude Re for the high-frequency correlated real signal and sums all of values in the imaginary high-frequency correlated signal 102 to provide an imaginary magnitude Im. The real and imaginary magnitudes are combined with one another in the same manner, using equation (2). The result is a value for the amplitude of the averaged, high-frequency signal which in turn represents the amplitude of the high-frequency component at $f_h$ in the impedance signal from detector 38. This amplitude in turn is directly related to the amount of $^{13}CO_2$ in the analyte within chamber 30. The value is entirely independent of the phase of signal 82 relative to the high-frequency modulation signal 70.

As described, for example, in the aforementioned U.S. Pat. No. 5,394,236, the disclosure of which is hereby incorporated by reference herein, the values representing the components in the impedance signals associated with $^{13}CO_2$ and $^{12}CO_2$ can be divided by one another and applied with a calibration constant to provide a value representing the ratio of $^{13}CO_2$ to $^{12}CO_2$ in the sample. The calibration content can be determined by operating the system with an analyte of known composition. The signals from each of the other sample units are processed in substantially in the same way. Where multiple samples are analyzed simultaneously, one of the samples may be a reference sample of known composition, so that the instrument can be calibrated simultaneously with measurements.

Numerous variations and combinations of the features set forth above can be utilized without departing from the present invention as defined by the claims. For example, a signal representing a particular frequency component in the impedance signal can be correlated with the real and imaginary correlation signals before averaging rather than after averaging. This cross-correlation can be performed either in the digital domain or in the analog domain. Analog domain cross-correlation can be performed by directing the impedance signal through two separate signal paths and modulating the gain of each signal path with one correlation signal. Each correlated analog signal can be digitized and the resulting digitized values can be captured and summed with values for other cycles. Once again, to provide averaging the value for each time within the correlated signal would be summed with other values offset by integral multiples of the period of the component in question. Also, the cross-correlation with each correlation signal can be performed in the digital domain prior to averaging by multiplying the digital values, as captured, by the corresponding values in a digitized correlation signal. The phase-independent amplitude value can be determined without use of the particular equation discussed above. For example, numerous cross-correlation signals differing slightly in phase from one another can be applied in the analog domain or in the digital domain to provide multiple cross-correlated signals, and the average magnitude of each cross-correlated signal can be determined. The highest average magnitude represents the magnitude obtained with a cross-correlation signal matched in phase to the component in the impedance signal, and thus represents the amplitude of the component in the impedance signal. Alternatively, the system can select component in the impedance signal varying at a particular frequency by filtering using an analog or digital frequency-selective filter such as a bandpass filter, and can generate a cross-correlation signal locked in phase with the selected component in the impedance signal using a feedback circuit such as a conventional phase-locked loop. The magnitude of the correlated signal obtained by cross-correlation of the selected component with such a correlation signal will be independent of the phase of the selected component in the impedance signal. In yet another alternative, each component in the impedance signal can be selected by a frequency-selective filter, amplified, rectified and integrated to yield a voltage which represents a value of the component magnitude.

Alternatively, other techniques for determining the amplitudes of signal components can be employed, provided that the result is substantially independent of the phase of the component in the impedance signal relative to the phase of the modulation signal used to drive the laser or other like source. For example, the impedance signal can be averaged and then subjected to Fourier transformation using conventional Fourier transformation algorithms. Such transformation will yield values for the magnitude and phase of the various components in the impedance signal. In another version, the system can subject the impedance signal to Fourier transformation and then average the resulting values. Also, although the preferred embodiments discussed above utilize multiple wavelengths and multiple modulation frequencies, the same techniques can be applied in systems where only a single wavelength is employed, using a single modulation frequency, so that the impedance signal includes only a single component of interest. Also, in the preferred arrangement discussed above, the component frequencies - - - the frequencies of the components in the impedance signal monitored by the system - - - are equal to the modulation frequencies. However, the modulation signal typically includes harmonics of the fundamental modulation frequencies. For example, a substantially square-wave modulation signal has substantial components at harmonics of its fundamental on/off frequency. The variation in the light from the laser will likewise include components at these harmonics and the impedance signal will also include components at the harmonics. Therefore, the system may utilize components in the impedance signal at harmonics of the fundamental frequency of the modulation signal.

The invention may be applied to optogalvanic spectroscopy of substances other than $^{13}CO_2$ and $^{12}CO_2$. Thus, the present invention can be applied to optogalvanic spectroscopy of essentially any substance, for determination of isotopic or chemical composition. As disclosed in the aforementioned U.S. Pat. No. 5,394,236, optogalvanic spectroscopy is particularly useful in the determining the isotopic composition of multiatomic moieties, such as molecules, multiatomic ions and multiatomic free radicals. The present invention can be applied in systems using these species. Moieties having less than 5 atoms, and most desirably 3 atoms or less, are particularly preferred. For example, the invention can be applied to determination of the isotopic composition of compounds such as CO, $CO_2$, NO, $N_2O$ and their respective ionized for, or of free ions such as OH containing various isotopes of carbon, oxygen and nitrogen.

As these and other variations and combinations of the features discussed above can be utilized without departing from the present invention, the foregoing description of the preferred embodiment should be taken by way of illustration rather than by way of limitation of the invention as defined by the claims.

What is claimed is:

1. A method of determining the composition of an analyte including the steps of:
   (a) maintaining the analyte in gaseous form in an electrical discharge;
   (b) applying first radiation to said analyte in said discharge so that said radiation interacts with a first species in said analyte to produce an optogalvanic effect;
   (c) monitoring electrical impedance of said discharge and providing an impedance signal representing said impedance;
   (d) periodically varying the amplitude of said first radiation at a first modulation frequency, whereby said impedance signal will include a first component varying at a first component frequency equal to the first modulation frequency or a harmonic thereof; and
   (e) detecting the amplitude of said first component to provide a first value representing said amplitude of said first component, whereby said first value represents the amount of said first species in said analyte, said detecting step being performed so that said value is substantially independent of the phase of said first component relative to the phase of said periodic variation in amplitude of said first radiation.

2. A method as claimed in claim 1 wherein said detecting step includes the step of correlating said first component with a pair of correlation signals varying at said first component frequency in quadrature with one another to thereby provide a first real correlated signal and a first imaginary correlated signal, determining the amplitudes of said correlated signals to provide a first real magnitude and a first imaginary magnitude, and combining said first real magnitude and said first imaginary magnitude to provide said first value.

3. A method as claimed in claim 2 wherein said combining step includes the step of computing $V_1=\sqrt{Re^2+Im^2}$ where $V_1$ is said first value, Re is said first real magnitude and Im is said first imaginary magnitude.

4. A method as claimed in claim 2 or claim 3 wherein said detecting step includes the steps of sampling said impedance signal at each of a succession of sampling times and providing a sample value for each said sampling time in digital form representing the impedance signal at such sampling time and storing said digital sample values.

5. A method as claimed in claim 4 wherein said detecting step further includes the step of digitally averaging sample values over a plurality of cycles of said first component of said impedance signal so that sample values for times delayed from one another by an integral number of periods of said first component are added to one another to thereby provide a set of averaged sample values representing an averaged cycle of said first component, each said averaged sample value being associated with a different time.

6. A method as claimed in claim 5 further comprising the step of providing each said correlation signal as a set of correlation signal values in digital form, each said correlation value in the set for one said correlation signal being associated with a different time, the step of correlating said first component with each said correlation signal including the step of digitally multiplying each said averaged sample value by the correlation value for such correlation signal associated with the same time as such averaged sample value to thereby provide a set of correlated values for each said correlation signal.

7. A method as claimed in claim 6 wherein said step of determining the magnitudes of said correlated signals includes the step of digitally summing the correlated values for each said correlated signal.

8. A method as claimed in claim 1 wherein said first component frequency is equal to said first modulation frequency.

9. A method as claimed in claim 1 further comprising the steps of:
   (a) applying second radiation to said analyte in said discharge so that said radiation interacts with a second species in said analyte to produce an optogalvanic effect;

(b) periodically varying the amplitude of said second radiation at a second modulation frequency, whereby said impedance signal will include a second component varying at a second component frequency equal to said second modulation frequency or a harmonic thereof; and (c) detecting the amplitude of said second component to provide a second value representing said amplitude of said second component, whereby said second value represents the amount of said second species in said analyte, said detecting step being performed so that said second value is substantially independent of the phase of said second component relative to the phase of said periodic variation in amplitude of said second radiation.

10. A method as claimed in claim 9 wherein said first and second species are multiatomic species.

11. A method as claimed in claim 10 wherein said first and second species have the same chemical composition but include different isotopes of the same element.

12. A method as claimed in claim 9 wherein said first and second species are carbon dioxide moieties including different isotopes.

13. A method as claimed in claim 9 wherein said first and second species are $^{13}CO_2$ and $^{12}CO_2$ moieties.

14. A method as claimed in claim 12 or claim 13 wherein said steps of providing said first and second radiation are performed by operating one or more carbon dioxide lasers.

15. A method as claimed in claim 9 further comprising the step of determining a relationship between amounts of said first and second species in said analyte by comparing said first and second values.

16. A method as claimed in claim 15 wherein said step of determining a relationship includes the step of determining a ratio between said first and second values.

17. Optogalvanic spectroscopy apparatus comprising:

(a) means for maintaining the analyte in gaseous form in an electrical discharge;

(b) means for applying first radiation to said analyte in said discharge so that said radiation interacts with a first species in said analyte to produce an optogalvanic effect;

(c) means for monitoring electrical impedance of said discharge and providing an impedance signal representing said impedance;

(d) means for periodically varying the amplitude of said first radiation at a first modulation frequency, whereby said impedance signal will include a first component varying at a first component frequency equal to the first modulation frequency or a harmonic thereof; and (e) means for detecting the amplitude of said first component to provide a first value representing said amplitude of said first component, whereby said first value represents the amount of said first species in said analyte, said detecting means being operative to detect said amplitude so that said value is substantially independent of the phase of said first component relative to the phase of said periodic variation in amplitude of said first radiation.

\* \* \* \* \*

UNITED STATES PATENT AND TRADEMARK OFFICE
CERTIFICATE OF CORRECTION

PATENT NO. : 5,706,082
DATED : January 6, 1998
INVENTOR(S) : Colgan, et. al.

It is certified that error appears in the above-identified patent and that said Letters Patent is hereby corrected as shown below:

Column 6, line 36, "544" should read --$54_1$--

Signed and Sealed this

Second Day of June, 1998

Attest:

BRUCE LEHMAN

*Attesting Officer*       *Commissioner of Patents and Trademarks*